(12) United States Patent
Punga et al.

(10) Patent No.: US 9,301,863 B2
(45) Date of Patent: Apr. 5, 2016

(54) PROSTHESIS DELIVERY APPARATUS AND METHODS

(75) Inventors: Karan Punga, Santa Rosa, CA (US); Christopher Bingham, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1785 days.

(21) Appl. No.: 12/400,867

(22) Filed: Mar. 10, 2009

(65) Prior Publication Data

US 2010/0234933 A1    Sep. 16, 2010

(51) Int. Cl.
*A61F 2/95* (2013.01)
*A61F 2/966* (2013.01)

(52) U.S. Cl.
CPC . *A61F 2/95* (2013.01); *A61F 2/966* (2013.01); *A61F 2002/9517* (2013.01)

(58) Field of Classification Search
CPC . A61F 2002/9522; A61F 2/2436; A61F 2/95; A61F 2/966; A61F 2002/9517
USPC .................. 606/200; 623/1.11, 1.12
See application file for complete search history.

(56) References Cited

U.S. PATENT DOCUMENTS

| | | | |
|---|---|---|---|
| 5,690,644 A * | 11/1997 | Yurek et al. | 623/1.11 |
| 5,709,703 A | 1/1998 | Lukic et al. | |
| 5,817,101 A * | 10/1998 | Fiedler | 623/1.11 |
| 6,113,608 A * | 9/2000 | Monroe et al. | 623/1.11 |
| 6,514,261 B1 | 2/2003 | Randall et al. | |
| 7,163,552 B2 | 1/2007 | Diaz | |
| 2001/0034549 A1 | 10/2001 | Bartholf et al. | |
| 2002/0032486 A1* | 3/2002 | Lazarovitz et al. | 623/23.67 |
| 2004/0093063 A1 | 5/2004 | Wright et al. | |
| 2007/0208350 A1 | 9/2007 | Gunderson | |

FOREIGN PATENT DOCUMENTS

| | | |
|---|---|---|
| EP | 0705578 | 4/1996 |
| EP | 1779818 | 5/2007 |
| EP | 1795223 | 6/2007 |

* cited by examiner

*Primary Examiner* — Katherine M Shi
*Assistant Examiner* — Michael Mendoza

(57) ABSTRACT

A self-expanding prosthesis delivery system having an outer tubular structure and an inner tubular structure adapted for tracking over a guidewire and disposed in the outer tubular structure where the outer tubular structure and inner tubular structure form a fluid fillable space, which when filled with a fluid forms a fluid column that provides column strength from the delivery system handle to the stop of the delivery system.

25 Claims, 8 Drawing Sheets

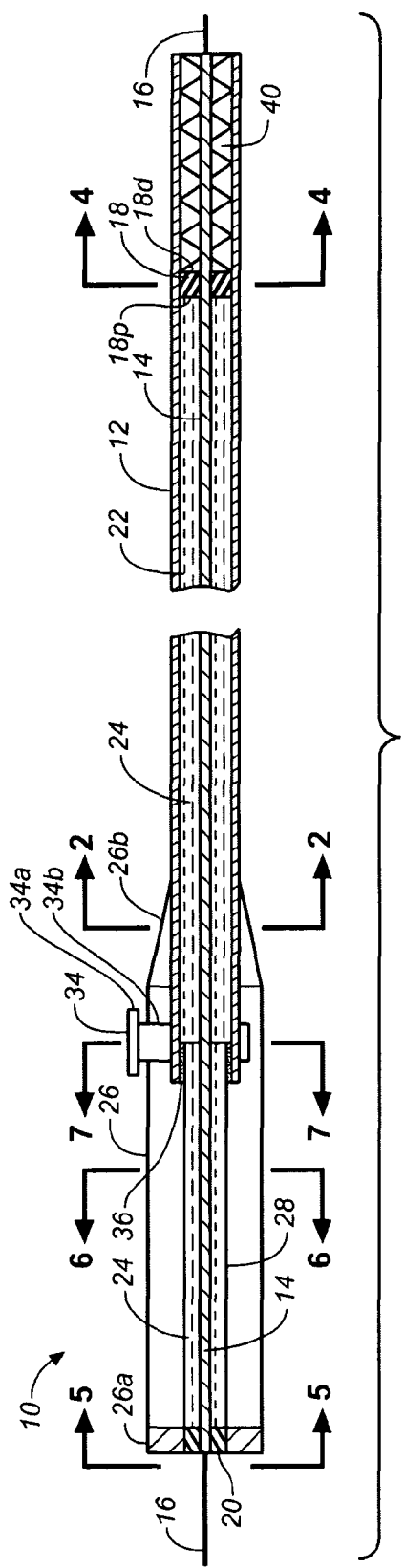
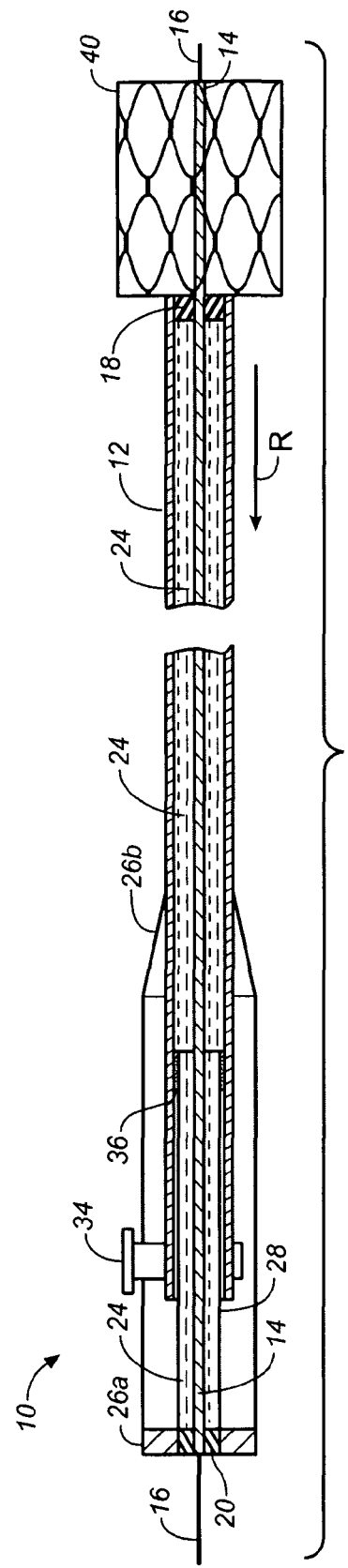

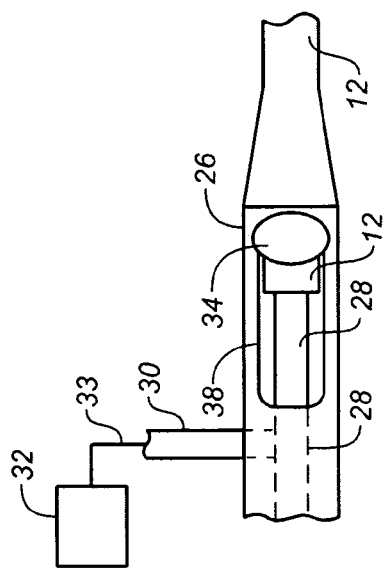
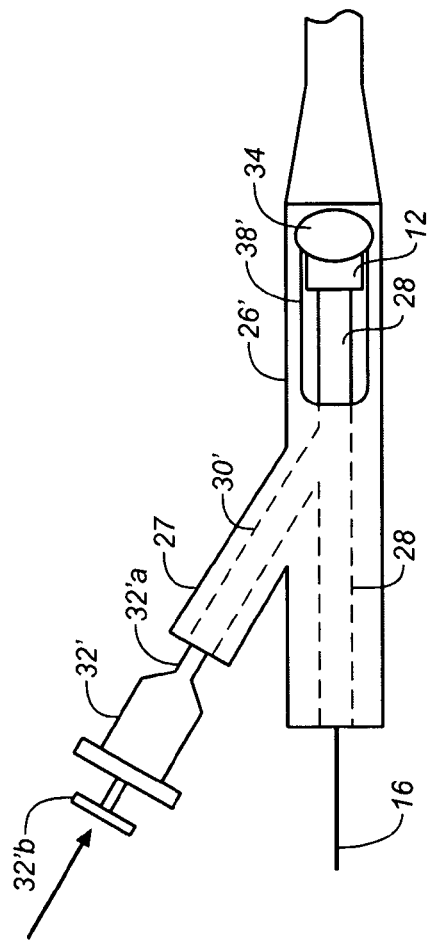

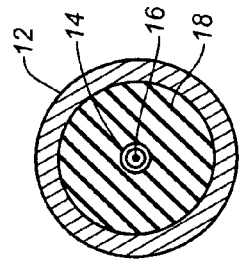
FIG. 4
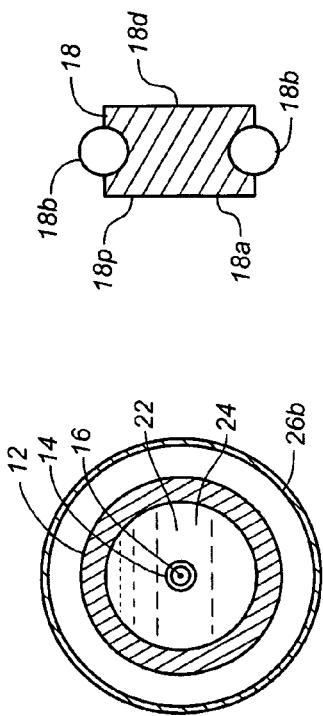
FIG. 3
FIG. 6
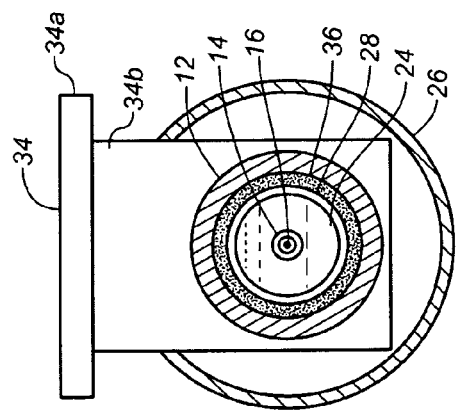
FIG. 2
FIG. 5
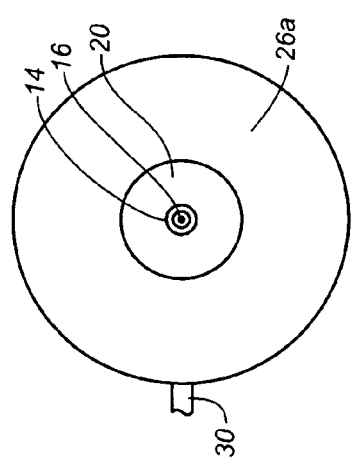
FIG. 7

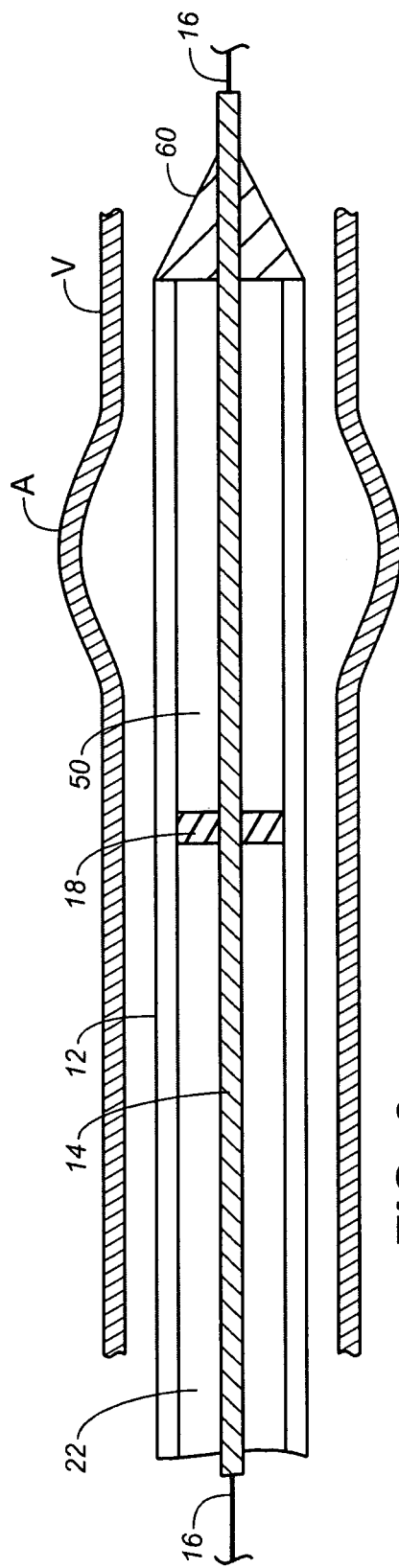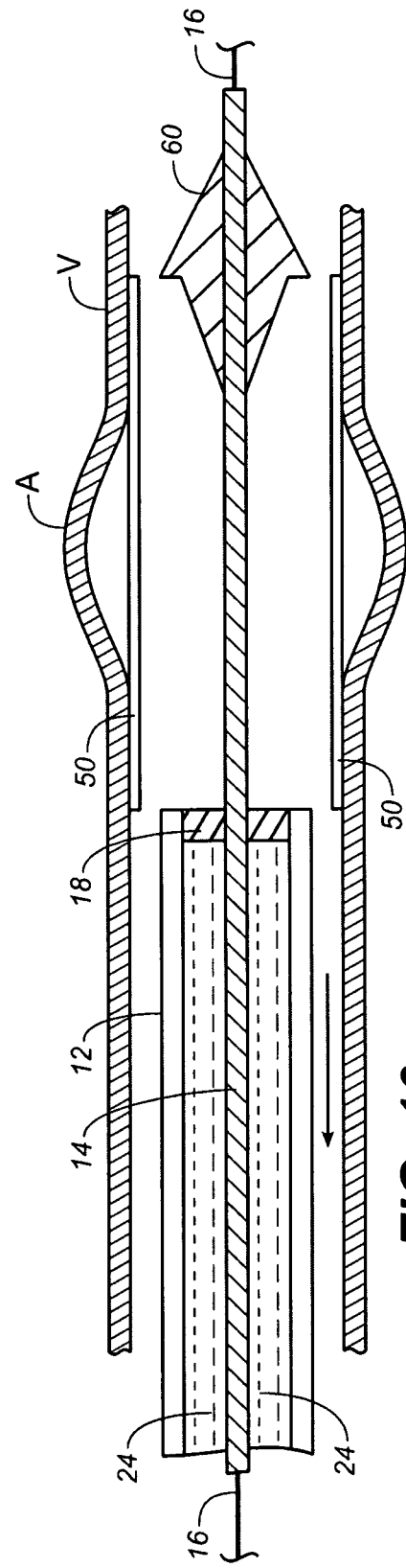

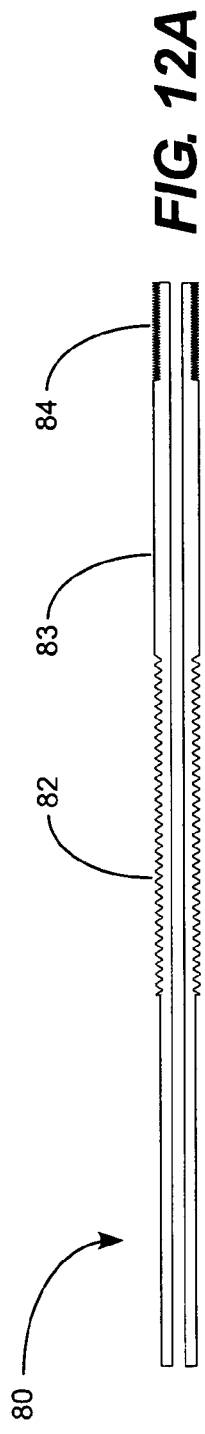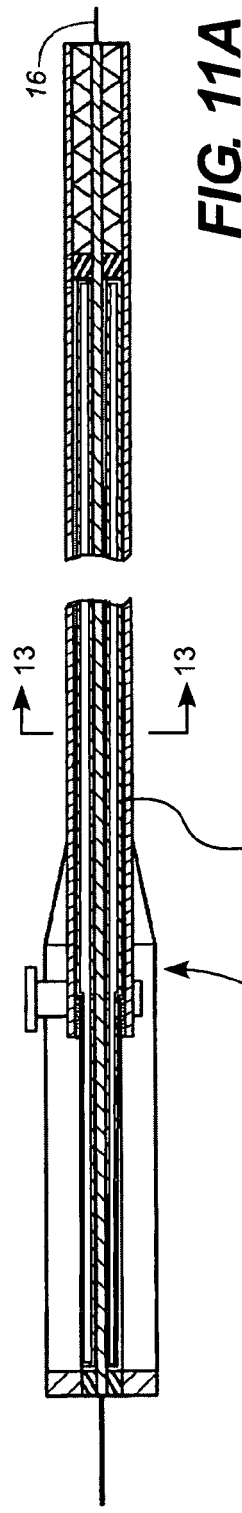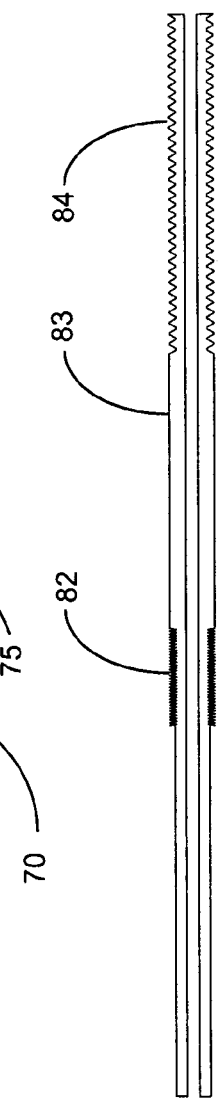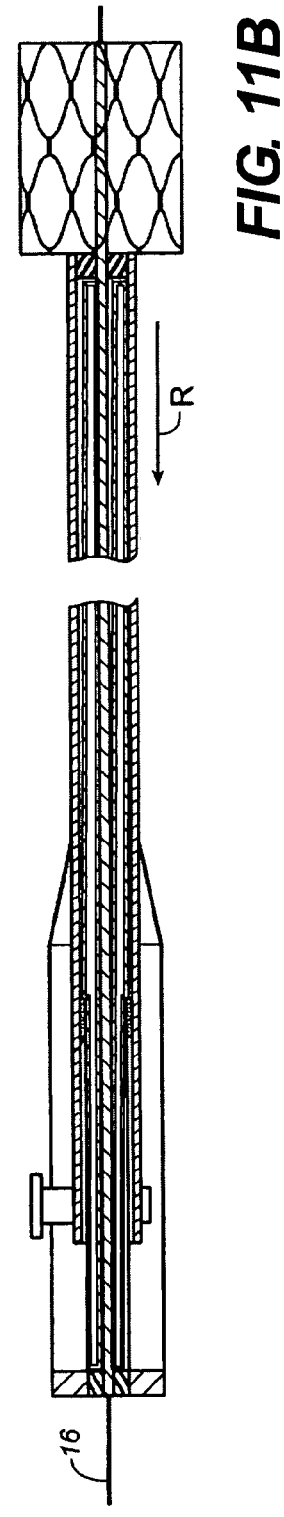

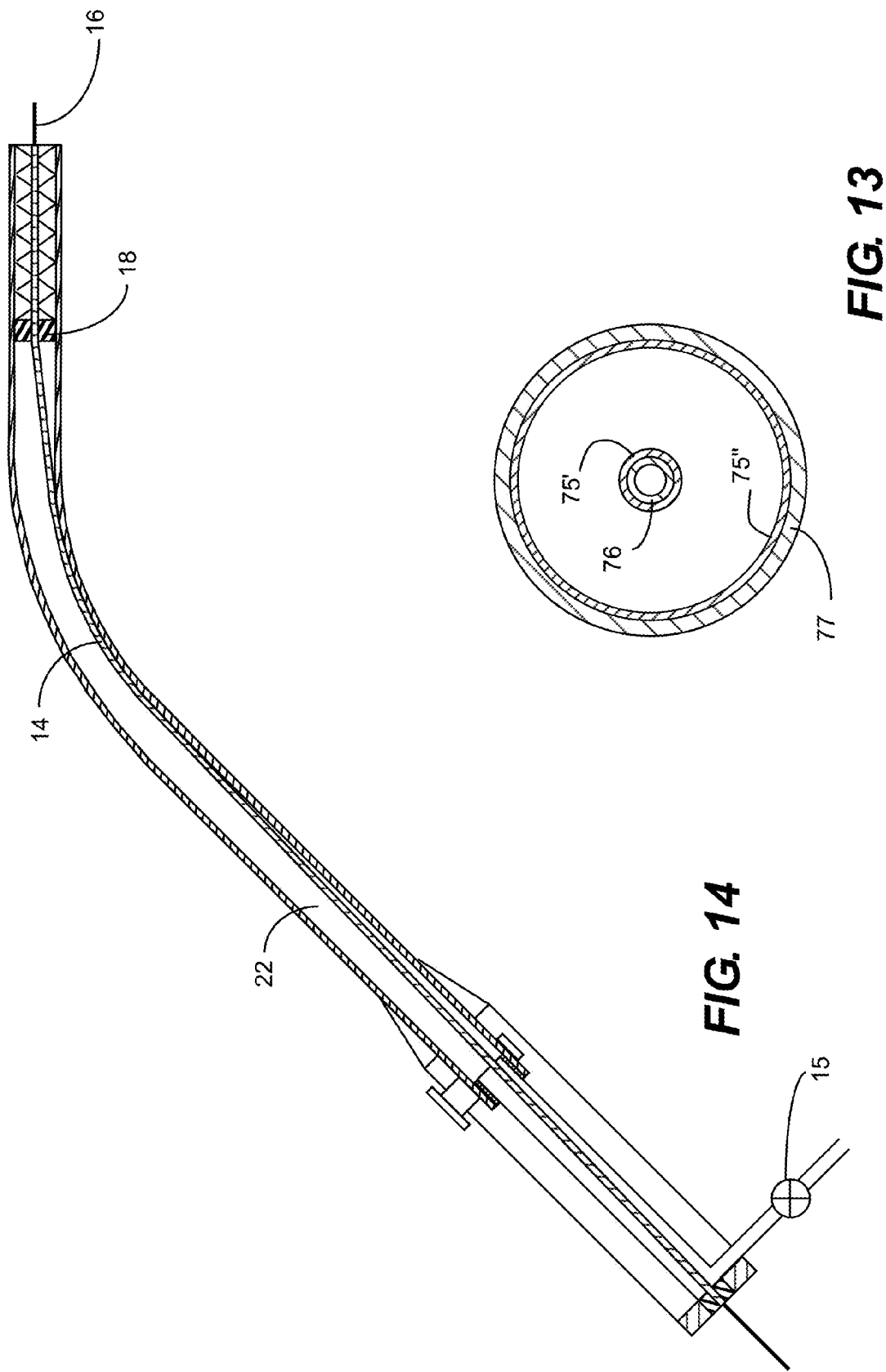

PROSTHESIS DELIVERY APPARATUS AND METHODS

FIELD OF THE INVENTION

The invention relates to prosthesis delivery in a passageway in a human body such as an artery.

BACKGROUND OF THE INVENTION

Tubular prostheses such as stents, grafts, percutaneous heart valves and stent-grafts (e.g., stents having an inner and/or outer covering comprising graft material and which may be referred to as covered stents) have been used to treat abnormalities in passageways in the human body. In vascular applications, these devices often are used to support, replace or bypass occluded, diseased or damaged blood vessels such as stenotic or aneurysmal vessels. Self-expanding or balloon expandable stents, for example, have been used to mechanically support vessels after angioplasty. It also is well known to use stent-grafts, which comprise biocompatible graft material (e.g., Dacron® material or expanded polytetrafluoroethylene (ePTFE) supported by a framework (e.g., one or more stent or stent-like structures) to treat or isolate aneurysms. The framework provides mechanical support and the graft material or liner provides a blood barrier.

Aneurysms generally involve abnormal widening of a duct or canal such as a blood vessel and generally appear in the form of a sac formed by the abnormal dilation of the duct or vessel wall. The abnormally dilated wall typically is weakened and susceptible to rupture. Aneurysms can occur in blood vessels such as in the abdominal aorta where the aneurysm generally extends below the renal arteries distally to or toward the iliac arteries.

In treating an aneurysm with a stent-graft, the stent-graft typically is placed so that one end of the stent-graft is situated proximally or upstream of the diseased portion of the vessel and the other end of the stent-graft is situated distally or downstream of the diseased portion of the vessel. In this manner, the stent-graft extends through the aneurysmal sac and beyond the proximal and distal ends thereof to replace or bypass the weakened portion. The graft material typically forms a blood impervious lumen to facilitate endovascular exclusion of the aneurysm.

Stents and stent-grafts can be implanted using a minimally invasive endovascular approach. In the case of an aneurysm, a minimally invasive endovascular stent-graft approach is preferred by many physicians over traditional open surgery techniques where the diseased vessel is surgically opened and a graft sutured into position such that it bypasses the aneurysm.

Minimally invasive endovascular approaches, which have been used to deliver stents, grafts, and stent-grafts, generally involve cutting through the skin to access a lumen of the vasculature. Alternatively, luminal or vascular access may be achieved percutaneously via successive dilation at a less traumatic entry point. Once access is achieved, the stent-graft can be routed through the vasculature to the target site. For example, a stent-graft delivery catheter loaded with a stent-graft can be percutaneously introduced into the vasculature (e.g., into a femoral artery) and the stent-graft delivered endovascularly across the aneurysm where it is deployed.

When using a balloon expandable stent-graft, balloon catheters generally are used to expand the stent-graft after it is positioned at the target site. When, however, a self-expanding stent-graft is used, the stent-graft generally is radially compressed or folded and placed at the distal end of a sheath or delivery catheter. Upon retraction or removal of the sheath or catheter at the target site, the stent-graft self-expands.

Many delivery catheters for delivering self-expanding devices such as stents or stent grafts have an inner, outer, and middle tube that are coaxially arranged for relative axial movement therebetween. The stent or stent-graft is radially compressed and positioned within the distal end of the outer tube (sheath) and in front of the distal end of the middle tube to which a stop is fixed. The stop, which is disposed between the middle tube and stent or stent-graft, resists proximal movement of the stent or stent-graft during retraction of the outer tube (sheath). The stop, which can be annular or disk shaped, includes a center opening through which the inner tube (or guidewire lumen) is slidably mounted. Once the catheter is positioned for deployment of the stent or stent-graft at the target site, the middle tube is held stationary and the outer tube (sheath) withdrawn so that the stent or stent-graft is gradually exposed and expands. All of these tubes are generally made out of extruded polymer braid tubes. Mechanically speaking, the column stiffness of the middle member should be sufficient to avoid buckling of the middle column during stent deployment.

Regarding proximal and distal positions referenced herein, the proximal end of a prosthesis (e.g., stent-graft) is the end closer to the heart (by way of blood flow) whereas the distal end is the end farther away from the heart during deployment. In contrast, the distal end of a catheter is usually identified as the end that is farthest from the operator, while the proximal end of the catheter is the end nearest the operator.

Although the endoluminal approach is much less invasive, and usually requires less recovery time and involves less risk of complication as compared to open surgery, there remains a need to improve delivery systems for endoluminal delivery through tortuous and/or small diameter vasculature.

SUMMARY OF THE INVENTION

The present invention involves improvements in prosthesis delivery.

In one embodiment according to the invention, a prosthesis delivery system comprises an outer tubular structure and an inner tubular structure adapted for tracking over a guidewire and disposed in the outer tubular structure where the outer tubular structure and inner tubular structure form a fluid fillable space, which when filled with a fluid forms a fluid column that provides column strength to the delivery system. Among the many advantages of this system is that the fluid column can eliminate the need for placing a tube between the inner and outer tubular structures, which tube may provide the system with more resistance to bending as compared to the fluid column.

In another embodiment according to the invention, a prosthesis delivery system comprises an at least partially moveable outer tubular structure; an inner tubular member adapted for tracking over a guidewire, having a proximal end portion and a distal end portion, and being disposed in the outer tubular structure; at least a portion of the outer tubular structure being movable relative to the inner tubular member such that at least a portion of the outer tubular structure can be retracted, while the inner tubular member provides a substantially fixed length core tension member; the outer tubular structure and inner tubular member being configured to be radially spaced from one another so as to form a fluid fillable space having first and second ends; a first seal fixedly secured to the inner tubular member at a location proximal to the distal end portion to fluidly seal one end of the fluid fillable space, the first seal extending from the inner tubular member to the outer tubular structure and being in sealing engagement with the outer tubular structure, the first seal having a first surface facing the distal end portion of the inner tubular member and a second surface facing the fluid fillable space; and a second seal arranged at the second end of the fluid fillable space to fluidly seal the second end of the fluid fillable space.

In another embodiment according to the invention, a prosthesis delivery system comprises an outer tubular structure; an inner tubular member adapted for tracking over a guidewire, having a proximal end portion and a distal end portion, and being disposed in the outer tubular structure; at least a portion of the outer tubular structure being movable relative to the inner tubular member such that at least a portion of the outer tubular structure can be retracted, while the axial position of the inner tubular member is held fixed; the outer tubular structure and inner tubular member being configured to be radially spaced from one another so as to form a fluid fillable space having first and second sealable ends; and a tube extending from the outer tubular structure and being fluidly coupled to the fluid fillable space for filling the fluid fillable space with a fluid.

In another embodiment according to the invention, a method of endoluminally positioning an endoluminal delivery system at a site in a human comprises endoluminally advancing to a desired site in a patient's lumen a prosthesis carrying delivery member, which comprises first and second tubular structures that form a fluid fillable space therebetween and a stop coupled to the first tubular structure and positioned at one end of the fluid fillable space where the stop is proximal to the prosthesis, extends radially from one of the tubular structures, and forms a seal between the first and second tubular structures; and providing a closed fluid filled space to the stop with a fluid column, while withdrawing at least a portion of the second tubular structure to expose the prosthesis.

In another embodiment according to the invention the inner and outer member can act as structural elements limiting the expansion of a toroidally shaped fluid filled bladder (or balloon) which can eliminate the need to construct fluid tight seals in the sliding contacts between the moving and stationary members around the stationary fluid filled column.

BRIEF DESCRIPTION OF THE DRAWINGS

FIG. 1A is a longitudinal sectional view of one prosthesis delivery system embodiment according to the invention before prosthesis deployment.

FIG. 1B illustrates the embodiment of FIG. 1A where the outer tubular sheath is retracted as indicated with arrow "R" and the prosthesis is deployed.

FIG. 1C is top view of the embodiment of FIG. 1.

FIG. 1D shows an alternative handle for the embodiment of FIG. 1

FIG. 2 is a sectional view taken along line 2-2 in FIG. 1

FIG. 3 is a side view of an example of a distal seal or stop shown in FIG. 1 with an O-ring.

FIG. 4 is a sectional view taken along line 4-4 in FIG. 1.

FIG. 5 is an end view taken from line 5-5 in FIG. 1.

FIG. 6 is a sectional view taken along line 6-6 in FIG. 1.

FIG. 7 is a sectional view taken along line 7-7 in FIG. 1.

FIGS. 9 and 10 illustrate delivering a prosthesis to bypass an aneurysm with the system illustrated in FIG. 1, where FIG. 9 shows positioning the prosthesis at the target site and FIG. 10 shows the tubular sheath of FIG. 1 retracted and the prosthesis deployed.

FIG. 11A is a longitudinal sectional view of one prosthesis delivery system with a bladder fluid containment system before prosthesis deployment.

FIG. 11B illustrates the embodiment of FIG. 11A where the outer tubular sheath is retracted as indicated with arrow "R" and the prosthesis is deployed.

FIGS. 12A and 12B are schematic sectional views showing an annular fluid containing bladder/balloon alone outside a catheter having corrugated expansion sections showing their respective pre-deployed and post deployed configuration pictured and oriented adjacent to and in alignment with the catheters pictured in FIGS. 11A and 11B.

FIG. 13 is a sectional view taken along line 13-13 in FIG. 11A

FIG. 14 is a longitudinal sectional view of the prosthesis delivery system illustrating the catheter in a curved configuration.

DETAILED DESCRIPTION

Figure 8:
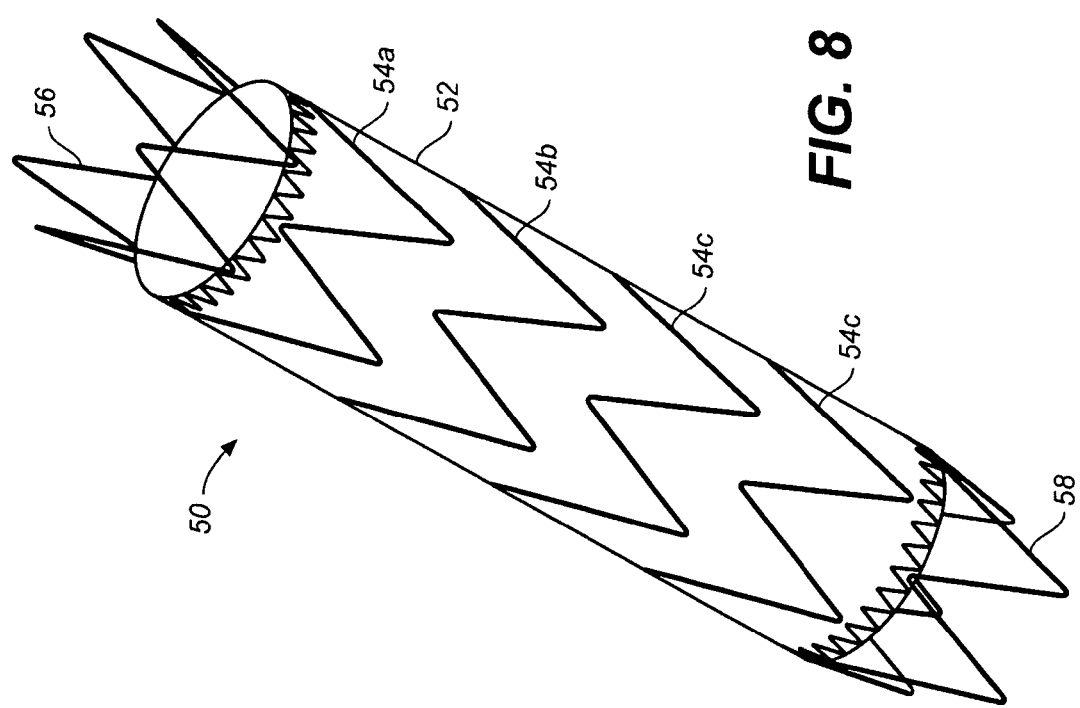
FIG. 8 is a diagrammatic perspective view of a stent-graft suitable for use with the embodiment of FIG. 1A.

The following description will be made with reference to the drawings where when referring to the various figures, it should be understood that like numerals or characters indicate like elements. Further, when referring to catheters and delivery devices described below, the proximal end is the end nearest the operator and the distal end is farthest from the operator.

According to one embodiment, a prosthesis delivery catheter comprises an outer tubular structure, having at least one retractable portion, and an inner tubular structure or member adapted to track over a guidewire. The outer tubular structure and inner tubular member are positioned to form a fluid fillable space. No middle tube is provided therebetween. When the fluid fillable space is filled with a fluid, a fluid column between the inner and outer tubes is formed. The fluid column provides sufficient column strength to assist with prosthesis deployment. The radial (hoop) stiffness of the inner and outer tubes prevents expansion of the fluid column to the extent necessary to generate the desired column strength. Conventional tubing such as tubing made from a polymer braid or hypotube can be used to make the aforementioned tubular elements. The fluid fillable chamber is generally filled before endoluminal delivery of the system or after the system is positioned with the prosthesis aligned with the target site. The two tube system provides a much lower crossing profile as compared to a traditional three tube system where the required middle/center member deployment column stiffness is derived from a middle tube disposed between a guidewire lumen and an outer tubular sheath and arranged to support a stop that abuts the prosthesis during deployment. Since the stiffness of the fluid column is almost negligible in bending, the system has much better trackability even when the fluid fillable chamber is filled with fluid prior to endoluminal delivery as compared to traditional three tube systems where the middle tube exhibits a bending stiffness. The deployment force is lower as compared to traditional three tube systems because there is minimal friction between the fluid column and outer tubular sheath as compared to some friction between an outer tube or sheath and a middle tube.

The various embodiments disclosed herein can be used, for example, to endoluminally or endovascularly deliver peripheral stents to the carotid, iliac, femoral, or superficial arteries, stent-grafts to the aortic or thoracic arteries, or to deliver heart valves to the heart or to deliver self expanding coronary stents which use outer sheaths over the stent.

Referring to FIG. 1A, one prosthesis delivery system embodiment according to the invention is shown. Prosthesis delivery system 10 generally comprises a prosthesis delivery catheter having an outer tubular member or sheath 12, inner tubular structure or member 14, which is adapted to track over guidewire 16, distal stop (sealing member) 18, which extends radially from inner tubular member 14 and forms a stop to minimize or prevent proximal movement of a prosthesis positioned distal thereto during deployment, tubular member 28, which can be a hypotube and which forms an extension of outer tubular member or tubular sheath 12, and a proximal sealing member such as proximal sealing member 20. When the catheter is linearly (as a straight line between two points) configured the outer tubular sheath 12 and inner tubular member 14 are configured as concentric tubes that are radially spaced from one another. Similarly, when the catheter is linearly configured, tubular member 28 and inner tubular member 14 are configured as concentric tubes that are radially spaced from one another. In this manner, outer tubular member or sheath 12 with its tubular extension (tubular member 28), which may be referred to as an outer tubular structure, inner tubular structure or member 14 and sealing members 18 and 20 form fluid fillable chamber 22, which can be filled with fluid such as a saline solution to form a tubular fluid column 24 that provides column strength to the system during positioning and deployment. This additional column strength minimizes or prevents system buckling when the outer sheath 12 is retracted during prosthesis deployment without the need for providing a tubular member between outer sheath 12 and inner tubular member 14. In the illustrative embodiment, nothing other than the fluid column is provided in fluid fillable chamber 22. While sealing members are shown and internal bladder or balloon could be used in lieu of sealing members.

In the illustrative embodiment (an idealized linear configuration), fluid fillable chamber 22 is annular and has a constant length during deployment because the distance between sealing members 18 and 20 is set by the tensioning of the inner tubular member 14 and does not change appreciably during deployment. When placed in a curved configuration the length of the chamber will change as discussed below. Once at the deployment location where the configuration of the catheter is set, the distance between sealing members 18 and 20 does not change from before prosthesis deployment (see e.g., FIG. 1A) to when outer tubular member or sheath 12 has been retracted to deploy the prosthesis (see e.g., FIG. 1B) where the distal end of outer tubular member or sheath 12 is aligned with sealing member 18. Accordingly, once fluid passages to the fluid column are closed the volume of fluid fillable chamber remains constant during prosthesis deployment.

Referring to FIGS. 1A and 1B, the prosthesis is a self-expanding stent (e.g., stent 40), while in FIGS. 8-10, the prosthesis is a self-expanding stent-graft (e.g., stent-graft 50). Referring to FIGS. 1A, 3, and 4, distal sealing member or stop 18 is annular, fixedly secured to inner tubular member 14 by, for example, gluing, and sized to form a seal with the inner wall surface of outer tubular member or sheath 12. Distal sealing member or stop 18 can be provided with one or more O-rings to enhance the seal as shown for example in FIG. 3 where a single O-ring embodiment is shown. More specifically, distal sealing member 18 includes an annular groove 18a into which an O-ring 18b is placed to enhance the seal between sealing member 18 and the inner wall surface of outer tubular member or sheath 12 when sheath 12 is retracted as will be described in more detail below. Alternately, an annular balloon molded in a shape to the inner cavity could be used which would obviate the need for special seals. Distal sealing member or stop 18 has a distal expanding surface 18d and a proximal surface 18p. Distal surface 18d abuts against one end of the radially compressed prosthesis, which typically is a self-expanding stent or stent-graft that is held in a radially compressed state in the region of the distal end portion of inner tubular member 18 and outer tubular member or sheath 12 by outer tubular member or sheath 12. Proximal surface 18p faces fluid chamber 22. A sectional view of the delivery system taken through sealing member or stop 18 is shown in FIG. 4.

Referring to FIGS. 1A and 2, the proximal end portion of outer tubular member or sheath 12 extends into an opening in the tapered distal end portion 26b of handle 26. At the other end of handle 26, proximal sealing member 20 is fixedly secured in the proximal portion 26a of handle 26, which has a bore in which sealing member 20 is secured as shown in FIGS. 1A, 1B, and 5. Proximal sealing member 20 can be secured to proximal portion 26a of handle 26 with any suitable means. For example, the interface between these elements can be glued or otherwise bonded together. Proximal sealing member 20 has a center bore through which inner tubular member 14 and guide wire 16 extend. In the illustrative embodiment, sealing member 20 is annular and sized with an outer diameter greater than that of tubular member 28 so that the inner circumference of sealing member 20 extends radially beyond the outer circumference of tubular member 28 to form a proximal fluid seal for tubular member 28 (see FIG. 5). Inner tubular member 14 extends through the axial bore in proximal sealing member 20 and is sized to form a fluid tight sealing engagement with proximal sealing member 20. The proximal end of tubular member 28 abuts and is sealingly secured to the distal face of proximal sealing member 20, which corresponds to the surface that faces chamber 22, using any suitable means such as glue.

Referring to FIG. 1A, the distal end portion of tubular member 28 extends into the proximal end portion of outer tubular member or sheath 12, which is slidably mounted over tubular member 28. Tubular member 28 forms an extension of outer tubular member or sheath 12 and together form an outer tubular structure whose overall length is adjustable or variable. FIG. 1A shows the outer tubular structure, which is formed by outer tubular member and tubular member 28, with a first length and FIG. 1B shows the outer tubular structure with a second length that is shorter than the first length due to retraction of outer tubular member or sheath 12 over tubular member 28. That is, outer tubular member or sheath 12 and tubular member 28 are slidable relative to one another. More specifically, since the proximal end of tubular member 28 is fixedly secured to handle 26, outer tubular member or sheath 12 can move axially relative to tubular member 28 and handle 26 while tubular member 28 and handle 26 are held stationary during, for example, retraction of while outer tubular member or sheath 12. Inner tubular member 14 also can be fixedly secured to proximal sealing member 20 so that it remains axially stationary relative to tubular member 28 and handle 26. Alternatively, inner tubular member 14 can be slidably mounted in proximal seal 20 and held axially stationary during deployment.

Referring to FIGS. 1A and 7, an annular sealing member 36 is fixedly secured to the distal end portion of tubular member 28 to provide a seal between tubular member 28 and the inner wall of outer tubular member or sheath 12. Sealing member 36 maintains the seal when outer tubular member or sheath 12 is retracted over tubular member 28 to deploy the prosthesis. Sealing member 36, which can be an O-ring, can be secured to the outer surface of tubular member 28 or embedded in a groove in tubular member 28 and can be fixed thereto with any suitable means such as glue.

The distal end of prosthesis delivery system 10 can be endoluminally delivered to the target site with chamber 22 filled with fluid or it can be filled with fluid after the distal end of outer tubular member or sheath 12 is positioned with the prosthesis aligned at the target site. The delivery system may be more suitable for delivery through tortuous and small diameter vasculature when in an unfilled state. An optional inlet/outlet port or tube 30, which can have an optional check valve (not shown) to control fluid flow in tube 30 (e.g., to allow fluid flow only in one direction), is shown in FIGS. 1C and 6, which can be used to fill fluid fillable chamber 22 before or after delivery to the target site and purge fluid from fluid fillable chamber 22 as desired, as is well known by persons skilled in the art for purging and filling balloons (e.g., PTCA balloons). In one variation, a valve (not shown) can be coupled to inlet/outlet port 30 or line 33 described below to allow fluid discharge when desired.

Referring to FIG. 6, an intermediate sectional view of handle 26 between sealing members 20 and 26 is shown illustrating an exemplary location for fluid inlet port or tube 30, which provides access to fluid filllable chamber 22. Fluid inlet port or tube 30 extends radially through a wall of handle 26 and through an opening in tubular member 28 to provide fluid to chamber 22. The end of fluid inlet port or tube 30 that extends into the wall of tubular member is sealingly secured to tubular member 28 to form a fluid tight attachment therebetween and can be welded, glued, or connected by any conventional means to tubular member 28 to provide such a connection. The other end of fluid inlet port or tube 30 is coupled to a fluid source 32 through line 33 as diagrammatically shown in FIG. 1C. In one embodiment, fluid source 32 can be a combined pump and fluid reservoir system. In this manner, fluid inlet port or tube 30 fluidly couples the fluid source to fluid fillable chamber 22 so that a fluid fillable chamber 22 can be filled with a fluid such as a saline solution. The fluid source can be configured to provide an initial desired fluid pressure in chamber 22, which can vary depending on system dimensions, such as the diameter and length of fluid fillable chamber 22, and the size and configuration of the prosthesis being deployed. In one example, the initial desired pressure in chamber 22 may range from about 5 psi to about 120 psi depending on the diameter and length of the fillable chamber 22 and the size and configuration of the prosthesis being deployed. Once ready for deployment the fluid chamber fill valve is closed (locking and setting the valume captured in the fluid filled chamber) and the retraction of the sheath can take place. When the fluid source is a fluid reservoir coupled to a pump, the pump output pressure can be preset in a desired range. In another variation, a sensor can be provided in fluid fillable chamber 22 and the pump provided with a controller to control pump output in response to the sensed pressure in fluid fillable chamber 22 to provide the desired fluid pressure therein. In another embodiment the fluid fillable chamber may be filled with a pressurized gas such that the gas pressure applies a force to the distal sealing member or stop 18 sufficient to overcome the frictional force applied to the distal sealing member as the sheath is retracted and the stent/stent graft is deployed and hold the stop 18 stationary with respect to the handle during deployment. A pressurized gas cartridge might be used as gas source, for example.

In another embodiment shown in FIG. 1D, a variation of handle 26 is shown and designated with reference number 26'. Handle 26' is the same as handle 26 with the exception that handle 26' includes proximally extending branch 27 through which fluid inlet port 30' extends to fluidly couple syringe 32' to fluid fillable chamber 22. Syringe 32' has a discharge outlet or needle 32'a, which is inserted into fluid inlet port or tube 30', and plunger 32'b, which forces fluid in syringe body 32'c through discharge outlet 32'a. Both handles 26 and 26' have a longitudinally extending slot 38 and 38', respectively, formed therein (FIGS. 1A, C, and 1D) to allow a slide 34 to move therein as will be described in more detail below.

Referring to FIGS. 1A, 1B, and 7 handle 26 and slide 34, which also can be referred to as a button, are shown in sectional views. Slide 34 has a finger portion or actuator 34a and a flange portion 34b extending therefrom. Flange portion 34b has an opening formed therethrough in which a proximal portion of outer tubular member or sheath 12 is fixedly secured by any suitable means such glue or heat fusion. With this construction, an operator can move slide 34, for example, between the position shown in FIGS. 1A and 1B. When slide 34 is moved from the position shown in FIG. 1A to that shown in FIG. 1B, while tubular member 28 and inner tubular member 14 with its sealing member or stop 18 are held in a fixed position, slide 34 carries with it outer tubular member or sheath 12 over tubular member 28 to withdraw the sheath from the prosthesis. The length of fluid fillable chamber 22 is not changed during this sheath withdrawal, which deploys the prosthesis. Stop 18 minimizes or prevents prosthesis movement in a proximal direction during sheath withdrawal. The fluid column 24 in fluid fillable chamber 22 provides axial support to distal sealing member or stop 18, which abuts the prosthesis (e.g., self-expanding stent 40) to resist proximal movement of the prosthesis during deployment. In the example in FIGS. 1A and 1B, the prosthesis is a self-expanding stent 40. Although a particular construction is shown in FIG. 1B, any suitable construction can be used.

Tubular members 12, 14, and 28 can be made from any suitable material such as extruded polymer braid tubes or hypotubes having a fluid impervious wall or walls that are at least fluid impervious to the fluid used (e.g., a saline solution) under the pressure used in the system. Sealing members 18, 20, and 36 can be made from any suitable sealing material as polyurethane, rubber, Teflon® made by DuPont or PTFE.

Referring to FIG. 8, an exemplary self-expanding stent-graft suitable for use with the system illustrated in FIG. 1 as an alternative to self-expanding stent 40 is schematically shown in a deployed state. Stent-graft 50 includes tubular graft material 52, which can be sewn to a support structure that provides support, strength, and stability to the stent-graft. Tubular graft material 52 can be made from any conventional graft material such Dacron® or expanded polytetrafluoroethylene (ePTFE) materials. In the illustrative example, the support structure comprises four undulating wire rings 54a,b,c,d. The wire rings can be nitinol and sewn to the graft material using polyester sutures. Stent-graft 50 also can have a support member (crown stent or spring 56) on the proximal end of the stent graft that is left mainly uncovered by the graft material. The uncovered portion typically will have a zig-zag like pattern with a predetermined number of apices protruding up. The apices form the extreme end of what is known as the proximal spring or crown 56. The distal end of stent-graft 50 also can have a crown or spring 58 having the same configuration as crown or spring 56.

Referring to FIGS. 9 and 10, an exemplary method of using prosthesis delivery system 10 is illustrated. Referring to FIG. 9, the distal portion of prosthesis delivery system 10 is endoluminally delivery to a target site in a vessel "V." In this example, radially compressed self-expanding stent-graft 50 is positioned within outer tubular member or sheath 12 distal to stop 18. The distal portion of prosthesis delivery system 10 is positioned so that stent-graft 50 is aligned with aneurysm "A." Chamber 22, which was not filled with a liquid during endolumenal delivery, is then filled with fluid and locked closed. Handle 26 with inner tubular member 14 are held stationary and actuator 34 moved proximally to move outer tubular member 12 proximally and unsheath stent-graft 50. In this manner, the stent graft is allowed to radially expand and assume the position shown in FIG. 10. An option distal nose 60 can be fixed to a distal portion of inner tubular member 14 as shown in FIGS. 9 and 10. Distal nose 60 serves as a distal cover of the distal end of outer tubular member or sheath 12. Distal nose 60 also permits the relatively larger diameter outer tubular member or sheath 12 to be moved within a patient's body, while minimizing the likelihood of sharp edges catching and damaging tissue.

Referring to FIGS. 11A, 11B, and 13, a prosthesis delivery system 70 is illustrated. The general details are as described earlier for with respect to FIGS. 1A and 1B. However in this instance, instead requiring tightly fitted catheter tubes and seals to prevent escape of fluid from the fluid fillable chamber, in this instance the fluid fillable chamber is lined with a sealed bladder or balloon 75. This bladder 75 would generally be an annular bladder constructed of an elastomer material sufficiently strong to retain the internal pressure in the across transition points in the wall of the surrounding fluid fillable chamber where leakage might otherwise occur. The annular shape permits the center member, e.g., 14, guiding the guidewire 16 to pass therethrough. The bladder or balloon 75 once positioning outside the center member (e.g., 14) and inside the sheath (e.g., 12) and tubular member (e.g., 28) between the distal end (sealing) member (e.g., 18) and the handle end and proximal end (sealing) member (e.g., 20). The outer diameter of the bladder is set by the internal surface of these respective pieces and the inner diameter is set by the outside surface diameter of the center member (e.g., 14). The bladder extends the full length from the handle to the stent stop/seal (e.g. 18) and is stationary though the sheath slides on its outside surface which has been made lubricious by use of a lubricious material such as PTFE.

FIG. 13 shows a cross section taken at 13-13 of FIG. 11A. The inner wall lining 75' and outer wall lining 75" are shown positioned against the center member 76 (e.g., 14) and sheath 77 (e.g., 12).

Alternately an annular bladder or balloon 80 having an outer layer with at least two expansion joint (accordion) sections a proximal expansion section 82 and a distal expansion section 84 on either side of a sheath static moveable section 83 as shown in their pre deployment configuration/arrangement in FIG. 12A and in their post deployment configuration in FIG. 12B. The sheath static moveable section 83 as shown in FIGS. 12A and 12B avoids the need for there to be sliding contact between the sheath (e.g., 12) and the outer wall of the bladder/balloon 80. Even using lubricious materials in tight spaces can create a static friction or sticktion that prevents readily sliding the sheath (e.g., 12) with respect to a static bladder 75 (FIGS. 11A and 11B). Using an annular bladder/balloon 80 with two outer surface corrugated sections 82, 84 as shown in FIGS. 12A and 12B can eliminate the static resistance to sliding that is present in the configurations of FIGS. 11A and 11B. The addition of corrugated (accordion like) expansion section 82. 84 on either side of a sheath static moveable section 83 which move with the sheath (e.g., 12) accommodates the linear axial motion of the sheath (e.g., 12) without the need to overcome the friction (however small it might be) between the outer surface of the bladder (e.g., 75) and the inner surface of the sheath (e.g., 12) while assuring that the liquid (incompressible fluid) in the fluid filled chamber is held tightly within the confines of the fluid filled chamber and any connecting tubing/piping to which it might be connected and locked closed by a closure valve or other suitable fluid stop.

FIG. 14 shows a stent delivery catheter according to the present invention in a curved configuration. The catheter configuration is the same as that shown in FIG. 1A, except that a fluid fill valve 15 is shown in a fluid filling passage connected to the fluid fillable chamber 22. While in this configuration the fluid passage and valve are shown entering from aside of the handle, the fluid passage to the static fluid column chamber could be at the proximal end of the handle or at any other suitable connection point that does not interfere with the retraction of the sheath (e.g., 12). In a curved configuration when the fluid fillable chamber 22 is pressurized, the pressure of the fluid will cause pressure in the chamber 22 to tend to stretch the chamber. The manifestation of this stretching causes the center member 14 to be stretched tight and move to the inside of the curve along which catheter is bent. Because this side movement of the center member can allow the distal end seal 18 to move slightly distally because of the tension in the center member, the volume of fluid contained in the fluid fillable chamber will be slightly increased. Therefore once the catheter is in position in curved or other configuration where the center member could be displaced from its center location, it is necessary to re-pressurize the fluid fillable chamber in that configuration and to lock closed the inlet valve of the fluid fillable chamber to hold the volume of the fluid fillable chamber constant so that maximum compressive force can be transmitted to the distal sealing member 18 from the handle, as retraction of the outer sheath is initiated to begin stent deployment. Once the fluid fillable chamber is fluid locked (fluid is prevent from exiting) the fluid in the chamber will act as an incompressible center compression member to carry the forces of deployment from the handle 26 to the distal sealing member 18.

Figure 15A:
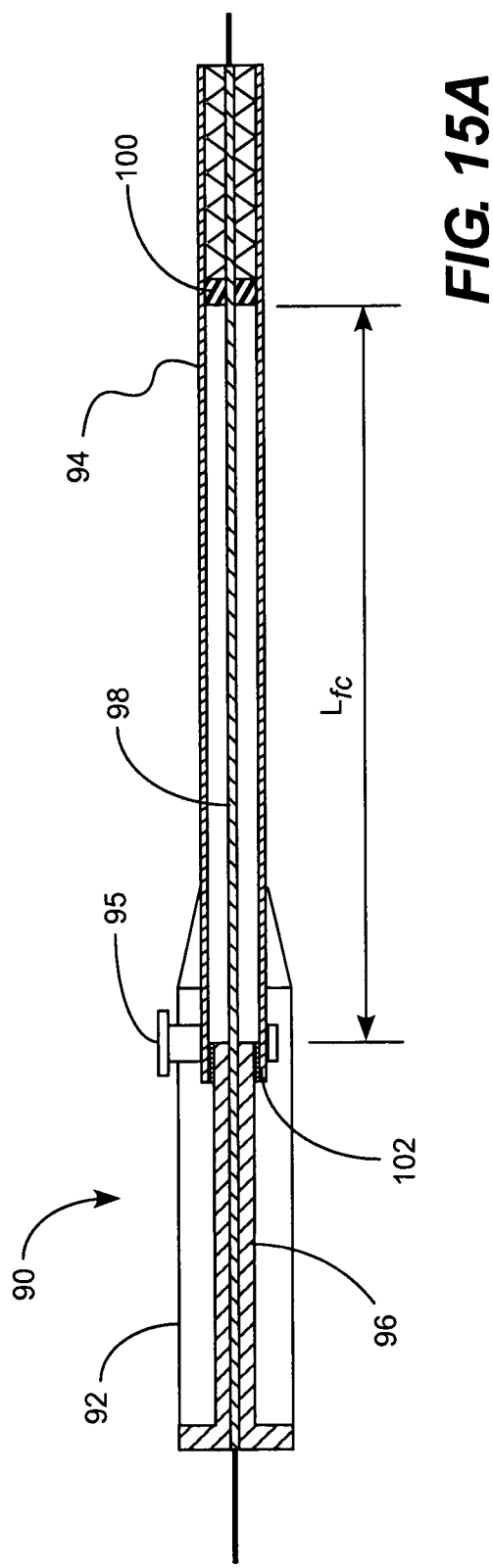
FIG. 15A is a longitudinal sectional view of one prosthesis delivery system having a fluid chamber length ($L_{fc}$) of the sheath extending between a distal seal/stop of the center member and the handle seal at a handle end of the center member as configured before prosthesis deployment.
Figure 15B:
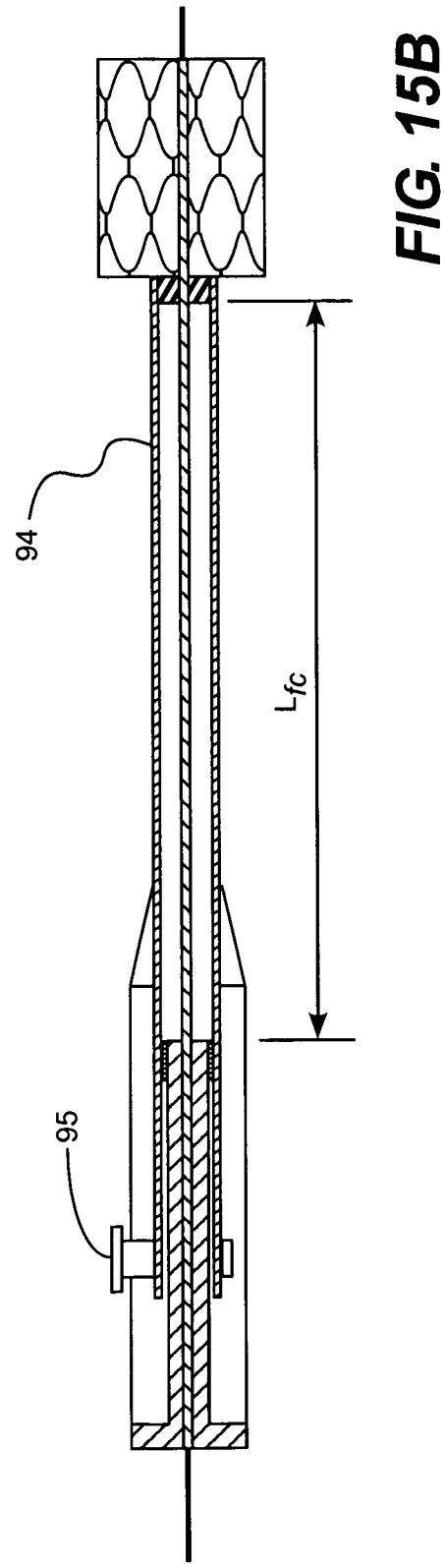
FIG. 15B illustrates the embodiment of FIG. 15A where the sheath has been retracted around the fluid chamber having a fluid chamber length ($L_{fc}$) to a position where the prosthesis has been deployed.

FIGS. 15A and 15B provide a sectional view of an alternate embodiment of a catheter using a static fluid column to transmit force to the stent stop at the distal end of the catheter. The catheter 90 is similar to that shown in FIGS. 1A and 1B. Rather than having a two piece tubular member, this embodiment has only one sliding element a sheath 94. At the proximal or handle end of the catheter, the sheath engages a handle sealing post (handle seal) 96 through which a center member 98 passes and is fixed. A distal portion of the center member is fixed to a distal sealing member 100. A sheath 94 having an actuator button 95 fixed thereto. The sheath 94 is configured to have its distal portion slide over the distal sealing member 100 with a fluid tight seal there between and its proximal portion slide over the distal portion of the sealing post 96 with a fluid tight seal 102 (as is well known in the art) there between The sheath 94 and the distal seal 100 and the proximal handle seal 102 create a fluid chamber having a length ($L_{fc}$) along the sheath extending between a distal seal/stop 100 of the center member and the handle seal 96 at a handle end of the center member 98r as configured before prosthesis deployment.

FIG. 15B illustrates the embodiment of FIG. 15A where the sheath has been retracted to a position where the prosthesis has been deployed. Here is can be seen that despite the movement of the sheath 94, the fluid chamber length ($L_{fc}$) remains unchanged as the fluid (incompressible liquid) column acts as a static compression member to prevent the distal seal/stop 100 from moving toward the handle 92 as the sheath 94 is retracted and the self-expanding prosthesis contained thereby is deployed.

Any feature described in any one embodiment described herein can be combined with any other feature of any of the other embodiments or features described herein. Furthermore, variations and modifications of the devices and methods disclosed herein will be readily apparent to persons skilled in the art.

What is claimed is:

1. A self-expanding prosthesis delivery system comprising:
    an outer tubular structure having a proximal end and a distal end configured to receive a self-expanding prosthesis;
    an inner tubular member adapted for tracking over a guidewire, having a proximal end portion fixed to a handle and a distal end portion, and being disposed in said outer tubular structure, at least a portion of said outer tubular structure being movable relative to said inner tubular member such that at least a portion of said outer tubular structure can be retracted, while said inner tubular member is held in a fixed position relative to said outer tubular structure, said outer tubular structure and inner tubular member being radially spaced from one another so as to form a fluid fillable space having first and second ends;
    a first sealing member fixedly secured to said inner tubular member at a location proximal to said distal end portion of said inner tubular member to fluidly seal said first end of said fluid fillable space, said first sealing member extending from said inner tubular member to said outer tubular structure and being in sealing engagement with said outer tubular structure even during deployment of a self-expanding prosthesis therefrom; and
    a second seal arranged at said second end of said fluid fillable space formed by said handle to fluidly seal said second end of said fluid fillable space,
    wherein said outer tubular structure, inner tubular member, first sealing member, and said second seal form a fluid fillable chamber, which has a constant volume that remains constant when said outer tubular structure is retracted a sufficient distance relative to said inner tubular member to deploy a self-expanding prosthesis.

2. The system of claim 1 wherein said fluid fillable space is includes a bladder lining said fluid fillable space.

3. The system of claim 2 wherein said bladder includes at least two longitudinal movement accommodating expansion sections operably coupled to said outer tubular structure by a movable section of said bladder,
    wherein said at least two longitudinal movement accommodating expansion sections are longitudinally expandable relative to said inner tubular member to thereby accommodate longitudinal movement between said outer tubular structure and said inner tubular member without sliding occurring between said outer tubular structure and said moveable section of said bladder, and
    wherein said movable section of said bladder moves in unison with said outer tubular structure and is disposed between said at least two longitudinal movement accommodating expansion sections.

4. The system of claim 1 wherein said fluid fillable chamber is filled with a liquid.

5. The system of claim 4 wherein said liquid is a saline solution.

6. The system of claim 1 further including a fluid inlet port extending from said outer tubular structure and being fluidly coupled to said fluid fillable chamber.

7. The system of claim 6 further including a fluid source coupled to said inlet port.

8. The system of claim 1 wherein said fluid fillable chamber is without another tubular member extending parallel to and between said inner tubular member and said outer tubular structure.

9. The system of claim 1 further including a self-expanding prosthesis disposed in said outer tubular structure in the region of said distal end portion of said inner tubular member and abutting said first sealing member.

10. The system of claim 9 wherein said self-expanding prosthesis is a stent.

11. The system of claim 9 wherein said self-expanding prosthesis is a stent-graft.

12. The system of claim 9 wherein said fluid fillable chamber in a deployment configuration has a constant length when at least a portion of said outer tubular structure is moved relative to said inner tubular member to deploy the self-expanding prosthesis.

13. The system of claim 1 wherein said fluid fillable chamber has a length, wherein during retraction of the outer tubular structure the sufficient distance to deploy a self-expanding prosthesis from the outer tubular structure when the fluid fillable chamber is filled with a liquid, the length of the fluid fillable chamber remains constant.

14. The system of claim 1 wherein the first sealing member is closer to the distal end of the outer tubular structure than the proximal end of the outer tubular structure.

15. A prosthesis delivery system comprising:
    an outer tubular structure;
    an inner tubular member adapted for tracking over a guidewire, having a proximal end portion fixed to a handle and a distal end portion, and being disposed in said outer tubular structure, at least a portion of said outer tubular structure being movable relative to said inner tubular member such that at least a portion of said outer tubular structure can be retracted to deploy a prosthesis, while said inner tubular member is held in a fixed position, said outer tubular structure and inner tubular member being radially spaced from one another so as to form a fluid fillable space having first and second sealable ends; and
    a tube extending from said outer tubular structure and being fluidly coupled to said fluid fillable space for filling said fluid fillable space with a fluid,
    wherein said first and second sealable ends of said fluid fillable space are sealed and said outer tubular structure, inner tubular member, and first and second sealed ends form a fluid fillable chamber which has a constant length when the at least a portion of said outer tubular structure is moved relative to said inner tubular member.

16. The system of claim 15 further including a first seal fixedly secured to said inner tubular member at a location proximal to said distal end portion to define said first sealed end of said fluid fillable chamber, said first seal extending from said inner tubular member to said outer tubular structure and being in sealing engagement with said outer tubular structure, said first seal having a first surface facing said distal end portion of said inner tubular member and a second surface facing said fluid fillable chamber.

17. The system of claim 16 further including a second seal as part of said handle to define said second sealed end of said fluid fillable chamber.

18. The system of claim 17 further including a prosthesis disposed in said outer tubular structure in the region of said distal end portion of said inner tubular member.

19. A prosthesis delivery system comprising:
an outer tubular structure;
an inner tubular member adapted for tracking over a guidewire, having a proximal end portion fixed to a handle and a distal end portion fixed to a first sealing member, and being disposed in said outer tubular structure, said outer tubular structure being movable relative to said first sealing member and said inner tubular member such that at least a portion of said outer tubular structure can be retracted, while said first sealing member and said inner tubular member are held in a fixed position, said outer tubular structure and inner tubular member being radially spaced from one another so as to form a fluid fillable space having first and second ends;
an annular bladder positioned within said outer tubular structure and outside said inner tubular member to fluidly seal said fluid fillable space between said first sealing member extending from said inner tubular member to said outer tubular structure and being in sliding contact with said outer tubular structure, said first sealing member having a first surface facing said distal end portion of said inner tubular member and a second surface facing and defining said second end of said fluid fillable space; and
a second seal arranged at said second end of said fluid fillable space to act as a closed support structure for the second end of said fluid fillable space.

20. The system of claim 19, wherein said annular bladder includes a corrugated section on it each of its inner and outer walls to permit axial stretching and contraction of the bladder.

21. The system of claim 19 wherein said bladder includes at least two longitudinal movement accommodating expansion sections operably coupled to said outer tubular structure by a movable section of said bladder,
wherein said at least two longitudinal movement accommodating expansion sections are longitudinally expandable relative to said inner tubular member to thereby accommodate longitudinal movement between said outer tubular structure and said inner tubular member without sliding occurring between said outer tubular structure and said moveable section of said bladder, and
wherein said movable section of said bladder moves in unison with said outer tubular structure and is disposed between said at least two longitudinal movement accommodating expansion sections.

22. A prosthesis delivery system comprising:
an inner tubular member having a proximal end and a distal end and having a guidewire passage therethrough, wherein said distal end of said inner tubular member is fixed to a distal stop and said proximal end of said inner tubular member is fixed to a handle; and
a tubular sheath having a proximal end and a distal end, wherein a proximal end of the sheath is slidably coupled to said handle, wherein at least a portion of said sheath surrounds and is slidable over each of a portion of said inner tubular member and said distal stop, where in a pre-deployed configuration a self-expanding prosthesis is held in a delivery configuration compressed within said distal end of said sheath distal to said distal stop, such that upon slidable retraction of said sheath over said distal stop, said distal stop is disposed to block retraction of the self-expanding prosthesis thereby causing the self-expanding prosthesis to be deployed and released from the distal end of said sheath,
wherein said distal stop, said tubular sheath, and said handle are sized and configured to create a substantially fluid tight fluid fillable chamber within said sheath between said distal stop and said handle with said inner tubular member passing therethrough, wherein a pressurized incompressible fluid fills said substantially fluid tight fluid fillable chamber, thereby carrying compressive load from said distal stop to said handle as said sheath is retracted to cause the self-expanding prosthesis to be deployed.

23. The system of claim 22, wherein said substantially fluid tight fluid fillable chamber is connected through a valve to a pressurized fluid source.

24. The system of claim 22, wherein said substantially fluid tight fluid fillable chamber includes an annular bladder lining which contains said pressurized incompressible fluid.

25. The system of claim 23, wherein said substantially fluid tight fluid fillable chamber includes an annular bladder lining which contains said pressurized incompressible fluid.

* * * * *